(12) United States Patent
Obara et al.

(10) Patent No.: US 10,791,973 B2
(45) Date of Patent: Oct. 6, 2020

(54) ANALYSIS DEVICE AND METHOD OF ANALYSIS

(71) Applicant: HOYA CORPORATION, Tokyo (JP)

(72) Inventors: Yoshimi Obara, Tokyo (JP); Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 180 days.

(21) Appl. No.: 16/095,880

(22) PCT Filed: Jul. 25, 2017

(86) PCT No.: PCT/IB2017/054489
§ 371 (c)(1),
(2) Date: Oct. 23, 2018

(87) PCT Pub. No.: WO2018/008008
PCT Pub. Date: Jan. 11, 2018

(65) Prior Publication Data
US 2019/0125229 A1    May 2, 2019

(30) Foreign Application Priority Data

Jul. 4, 2016 (JP) ................................. 2016-132619

(51) Int. Cl.
*A61B 5/1455* (2006.01)
*A61B 1/00* (2006.01)
(Continued)

(52) U.S. Cl.
CPC ............ *A61B 5/14552* (2013.01); *A61B 1/00* (2013.01); *A61B 1/045* (2013.01); *A61B 1/05* (2013.01);
(Continued)

(58) Field of Classification Search
CPC .............. A61B 5/1455; A61B 5/14551; A61B 5/14552; A61B 5/1459; A61B 5/743; A61B 5/7246; A61B 1/0638; A61B 1/0646
See application file for complete search history.

(56) References Cited

U.S. PATENT DOCUMENTS 5,512,940 A * 4/1996 Takasugi ............... G06T 7/0012
348/30
2012/0116192 A1    5/2012 Saito
(Continued)

FOREIGN PATENT DOCUMENTS

EP    2912991 A1    9/2015
EP    2992805 A1    3/2016
(Continued)

OTHER PUBLICATIONS

DE 11 2017 003 367.5, "Examination Report" dated Dec. 18, 2019, with English Translation.
(Continued)

*Primary Examiner* — Eric F Winakur
(74) *Attorney, Agent, or Firm* — Kilpatrick Townsend & Stockton LLP

(57) ABSTRACT

An analysis device includes a wavelength selection unit that alternatively extracts first special light and second special light from light emitted from the light source device, an image sensor that includes a RGB color filter, and a signal processing unit. In this configuration, the first special light includes light in a first wavelength region and the second special light includes light in a second wavelength region that is different from the first wavelength region. The signal processing unit calculates an indicator that indicates a feature amount of biological tissue based on a pixel signal that corresponds to the light in the first wavelength region and a pixel signal that corresponds to the light in the second
(Continued)

wavelength region, and generates a color captured image based on a pixel signal that corresponds to light that passes through the RGB color filter.

20 Claims, 9 Drawing Sheets

(51) Int. Cl.
*A61B 1/045* (2006.01)
*A61B 1/05* (2006.01)
*A61B 1/06* (2006.01)
*A61B 5/00* (2006.01)
*A61B 5/1459* (2006.01)
*G01N 21/31* (2006.01)
*G06T 7/00* (2017.01)

(52) U.S. Cl.
CPC .......... *A61B 1/0638* (2013.01); *A61B 1/0646* (2013.01); *A61B 5/0075* (2013.01); *A61B 5/1459* (2013.01); *A61B 5/7246* (2013.01); *A61B 5/743* (2013.01); *G01N 21/314* (2013.01); *G06T 7/0014* (2013.01); *G01N 2021/3144* (2013.01); *G06T 2207/10068* (2013.01); *G06T 2207/30024* (2013.01)

(56) References Cited

U.S. PATENT DOCUMENTS

| | | | |
|---|---|---|---|
| 2012/0253157 A1* | 10/2012 | Yamaguchi | A61B 5/1459 600/328 |
| 2014/0100427 A1* | 4/2014 | Saito | A61B 5/1459 600/178 |
| 2015/0238126 A1 | 8/2015 | Saito | |
| 2016/0120449 A1 | 5/2016 | Chiba | |
| 2016/0146723 A1 | 5/2016 | Chiba | |
| 2017/0167980 A1* | 6/2017 | Dimitriadis | A61B 5/14551 |

FOREIGN PATENT DOCUMENTS

| | | |
|---|---|---|
| EP | 3023050 A1 | 5/2016 |
| JP | 5231511 B2 | 7/2013 |
| JP | 2015-177961 A | 10/2015 |
| JP | 2016-97067 A | 5/2016 |
| WO | 2014192781 A1 | 12/2014 |

OTHER PUBLICATIONS

PCT/IB2017/054489, "International Search Report and Written Opinion", dated Oct. 31, 2017, 7 pages.
DE 11 2017 003 36735, "Examination Report" dated Dec. 18, 2019, with English Translation.

* cited by examiner (3A) (3B)

(4A) (4B)

(5A) (5B)

(a)

(b)

ANALYSIS DEVICE AND METHOD OF ANALYSIS

CROSS-REFERENCE TO RELATED APPLICATIONS

This application is a 371 U.S. National Phase of PCT International Application No. PCT/IB2017/054489, filed on Jul. 25, 2017, which claims benefit and priority to Japanese patent application No. 2016-132619, filed on Jul. 4, 2016. Both of the aforementioned applications are incorporated by reference herein in their entirety.

TECHNICAL FIELD

The present disclosure relates to an analysis device that acquires biological information such as the concentration of a biological substance in biological tissue based on a captured image of the biological tissue.

BACKGROUND ART

An endoscope device is known that includes a function for determining the quantity of a biological substance (e.g., total hemoglobin amount) in biological tissue that is the imaging subject, based on color information in an endoscopic image. One example of such an endoscope device is disclosed in WO 2013/192781 (hereinafter, called "Patent Document 1").

The endoscope device disclosed in Patent Document 1 calculates an indicator that indicates the total hemoglobin amount and an indicator that indicates the degree of oxygen saturation, based on three captured images obtained by irradiating biological tissue with three types of illumination light that have different wavelength regions, and capturing images of the biological tissue irradiated with the respective types of illumination light. Also, a color captured image of the biological tissue is obtained by irradiating the biological tissue with white illumination light.

SUMMARY OF DISCLOSURE

In order to calculate the indicators that indicate the total hemoglobin amount and the degree of oxygen saturation, and to acquire the color captured image, the endoscope device disclosed in Patent Document 1 successively irradiates the subject with four types of illumination light and captures respective images. For this reason, there has been a problem that the frame rate of the obtained color captured images decreases to ¼ of the frame rate in the case of irradiating the subject with only white light.

The present disclosure was achieved in light of the above-described circumstances, and an object of the present disclosure is to provide an analysis device that can perform spectroscopic analysis while also suppressing a reduction in the captured image frame rate.

According to an aspect of the present disclosure, an analysis device includes: a light source device; a wavelength selection unit that alternatively extracts first special light and second special light from light emitted from the light source device, the first special light and the second special light having mutually different spectrums; an image sensor that includes an RGB color filter, receives light from a biological tissue that is a subject, and outputs a pixel signal that corresponds to the received light; and a signal processing unit that performs predetermined signal processing on the pixel signal output from the image sensor. In this configuration, the first special light includes light in a first wavelength region that passes through a G filter of the RGB color filter, the second special light includes light in a second wavelength region that passes through the G filter, the second wavelength region being different from the first wavelength region, at least one of the first special light and the second special light includes light that passes through an R filter of the RGB color filter, and at least one of the first special light and the second special light includes light that passes through a B filter of the RGB color filter. Also, the signal processing unit calculates a first indicator that indicates a feature amount of the biological tissue, based on the pixel signal output according to the light in the first wavelength region and the pixel signal output according to the light in the second wavelength region, and the signal processing unit generates a color captured image of the biological tissue based on the pixel signal output according to light that passes through the RGB color filter.

According to this configuration, the biological tissue is alternatively irradiated with the first special light and the second special light. Also, the pixel signal output according to the light in the first wavelength region and the pixel signal output according to the light in the second wavelength region are used to calculate a feature amount of the biological tissue and also to generate a color captured image of the biological tissue. In this way, the calculation of a feature amount of the biological tissue and the generation of a color captured image are performed using two types of light, thus making it possible to suppress a reduction in the frame rate of color captured images in comparison with conventional technology.

Also, according to an aspect of the present disclosure, the feature amount is a degree of oxygen saturation of hemoglobin included in the biological tissue, for example. In this configuration, the first indicator is a ratio N/W of a pixel signal N output from the image sensor according to the light in the first wavelength region and a pixel signal W output from the image sensor according to the light in the second wavelength region.

Also, according to an aspect of the present disclosure, the first wavelength region includes a wavelength region that is defined by a predetermined pair of isosbestic points of hemoglobin, and the second wavelength region includes a wavelength region that includes the first wavelength region and is defined by a pair of isosbestic points that is different from the predetermined pair of isosbestic points of hemoglobin, for example.

Also, according to an aspect of the present disclosure, the first wavelength region is a wavelength region of wavelengths greater than or equal to 546 nm and less than or equal to 570 nm, and the second wavelength region is a wavelength region of wavelengths greater than or equal to 528 nm and less than or equal to 584 nm, for example.

Also, according to an aspect of the present disclosure, a wavelength region of light transmitted by the R filter includes a wavelength region of wavelengths greater than or equal to 600 nm, a wavelength region of light transmitted by the G filter includes a wavelength region of wavelengths greater than or equal to 528 nm and less than or equal to 584 nm, and a wavelength region of light transmitted by the B filter includes a wavelength region of wavelengths less than or equal to 502 nm, for example.

Also, according to an aspect of the present disclosure, the signal processing unit calculates a second indicator that indicates the amount of hemoglobin included in the biological tissue, using the following expression, based on the pixel signal W, a pixel signal R output from the image sensor according to light that passes through the R filter, and a pixel signal B output from the image sensor according to light that passes through the B filter,

W/(C1×R+C2×W+C3×B)

where C1, C2, and C3 are each a constant greater than or equal to zero, for example.

Also, according to an aspect of the present disclosure, the signal processing unit generates a color captured image of the biological tissue based on a pixel signal R output from the image sensor according to light that passes through the R filter, a pixel signal G output from the image sensor according to light that passes through the G filter, and a pixel signal B output from the image sensor according to light that passes through the B filter, for example. In this configuration, the pixel signal G is one of a pixel signal N output from the image sensor according to the light in the first wavelength region and a pixel signal W output from the image sensor according to the light in the second wavelength region.

Also, according to an aspect of the present disclosure, the wavelength selection unit includes a first optical filter that extracts the first special light from the light emitted from the light source device, a second optical filter that extracts the second special light from the light emitted from the light source device, and a filter drive unit that alternatively inserts the first optical filter and the second optical filter into a light path of the light emitted from the light source device, for example.

A configuration of an aspect of the present disclosure provides an analysis device that can perform spectroscopic analysis while also suppressing a reduction in the captured image frame rate.

DESCRIPTION OF EMBODIMENTS

Hereinafter, an embodiment of the present disclosure will be described with reference to the drawings. An endoscope device according to an embodiment of the present disclosure described below is a device for quantitatively analyzing biological information of a subject (e.g., a feature amount of biological tissue such as the total hemoglobin amount or the degree of oxygen saturation) based on images captured using illumination with light having different wavelength regions, and for converting the analysis results into an image and displaying the image. The spectral characteristics of blood (i.e., the spectral characteristics of hemoglobin) have a property of continuously varying according to the total hemoglobin amount and the degree of oxygen saturation, and this property is used in the quantitative analysis of the total hemoglobin amount and the degree of oxygen saturation described below.

Spectral characteristics of biological tissue and principle of calculation of biological information Before giving a description of the detailed configuration of the endoscope device according to the present disclosure, the following describes the spectral characteristics of hemoglobin and the principle of the calculation of a feature amount of biological tissue (biological information), such as the degree of oxygen saturation, according to the present disclosure. Hemoglobin includes oxygenated hemoglobin (HbO2) and reduced hemoglobin (Hb), and the percentage of oxygenated hemoglobin is called the degree of oxygen saturation. The spectral characteristics of hemoglobin vary according to the degree of oxygen saturation.

Figure 1:
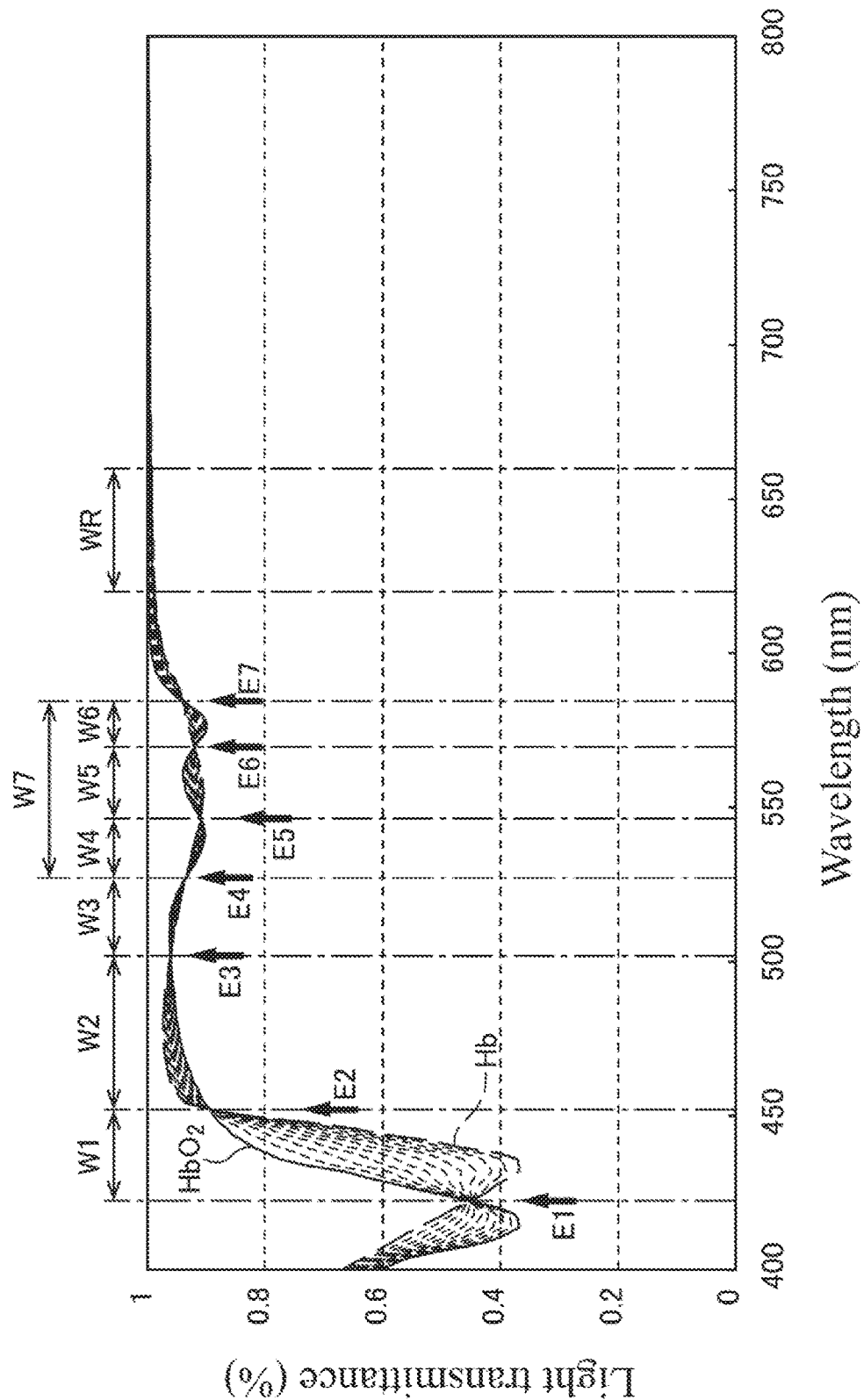
FIG. 1 shows the transmission spectrum of hemoglobin.

FIG. 1 shows the transmission spectrum of hemoglobin. In FIG. 1, the horizontal axis indicates the wavelength of light, and the vertical axis indicates the light transmittance T (%). The transmission spectrum of hemoglobin varies according to the degree of oxygen saturation. The solid line waveform in FIG. 1 is the transmission spectrum in the case where the degree of oxygen saturation is 100% (i.e., oxygenated hemoglobin $HbO_2$), and the long dashed line waveform is the transmission spectrum in the case where the degree of oxygen saturation is 0% (i.e., reduced hemoglobin Hb). Also, the short dashed lines are the transmission spectrums of hemoglobin (mixtures of oxygenated hemoglobin $HbO_2$ and reduced hemoglobin Hb) at intermediate degrees of oxygen saturation (10, 20, 30, . . . 90%).

Note that the absorption (light absorption) A of hemoglobin is calculated based on the light transmittance T, using Expression 1 below.

$$A = -\log T \qquad \text{Expression 1}$$

As show the transmission spectrum of hemoglobin includes isosbestic points E1 (424 nm), E2 (452 nm), E3 (502 nm), E4 (528 nm), E5 (546 nm), E6 (570 nm), and E7 (584 nm) at which the light transmittance (i.e., absorption A) is constant regardless of the degree of oxygen saturation. In this specification, the wavelength region between the isosbestic points E1 and E2 is defined as a wavelength region W1, the wavelength region between the isosbestic points E2 and E3 is defined as a wavelength region W2, the wavelength region between the isosbestic points E3 and E4 is defined as a wavelength region W3, the wavelength region between the isosbestic points E4 and E5 is defined as a wavelength region W4, the wavelength region between the isosbestic points E5 and E6 is defined as a wavelength region W5, and the wavelength region between the isosbestic points E6 and E7 is defined as a wavelength region W6. Also, the wavelength region from the wavelength of 620 nm to the wavelength of 660 nm is defined as a wavelength region WR. Furthermore, in the following description in this document, the wavelength region W5 is also called the N band (Narrow band). Moreover, the wavelength region between the isosbestic points E4 and E7 is also called the W band (Wide band).

As shown in FIG. 1, in the regions between adjacent isosbestic points, the light transmittance T of hemoglobin increases or decreases linearly relative to the degree of oxygen saturation. For example, light transmittances $T_{W4}$ and $T_{W6}$ of hemoglobin in the wavelength regions W4 and W6 increase linearly relative to the concentration of reduced hemoglobin. Also, the light transmittance $T_{W5}$ of hemoglobin in the wavelength region W5 increases linearly relative to the concentration of oxygenated hemoglobin.

Here, the degree of oxygen saturation is defined by Expression 2 below.

$$Sat=[HbO_2]/([Hb]+[HbO_2]) \qquad \text{Expression 2}$$

where
Sat: degree of oxygen saturation
[Hb]: concentration of reduced hemoglobin
[HbO$_2$]: concentration of oxygenated hemoglobin
[Hb]+[HbO$_2$]: total hemoglobin amount (tHb)

Also, Expression 3 and Expression 4 that express the concentrations of oxygenated hemoglobin HbO$_2$ and reduced hemoglobin Hb are obtained from Expression 2.

$$[HbO_2]=Sat\times([Hb]+[HbO_2]) \qquad \text{Expression 3}$$

$$[Hb]=(1-Sat)\times([Hb]+[HbO_2]) \qquad \text{Expression 4}$$

Accordingly, the light transmittances $T_{W4}$, $T_{W5}$, and $T_{W6}$ of hemoglobin are characteristic amounts that are dependent on both the degree of oxygen saturation and the total hemoglobin amount.

Also, through examination performed by the patent applicants, it was found that an integrated value $T_{W7}$ of the light transmittance of hemoglobin in the wavelength region W7, which is made up of the wavelength regions W4, W5, and W6, is a value that is determined by the total hemoglobin amount and is not dependent on the degree of oxygen saturation.

Accordingly, the total hemoglobin amount can be determined based on the light transmittance $T_{W7}$. Also, the degree of oxygen saturation can be determined based on the light transmittance $T_{W4}$, $T_{W5}$, or $T_{W6}$, along with the total hemoglobin amount determined based on the light transmittance $T_{W7}$. More specifically, it is possible to obtain an indicator value that expresses the total hemoglobin amount and the degree of oxygen saturation. As shown in FIG. 1, among the wavelength regions W4, W5, and W6, the amount of variation in the light transmittance according to the degree of oxygen saturation (i.e., the area of the region surrounded by the solid line waveform and the long dashed line waveform) is the largest in the wavelength region W5, and the light transmittance $T_{W5}$ in the wavelength region W5 is a characteristic amount that is highly sensitive to the degree of oxygen saturation. In another embodiment described later, the degree of oxygen saturation is determined using light in the wavelength region W5 (N band).

Figure 2:
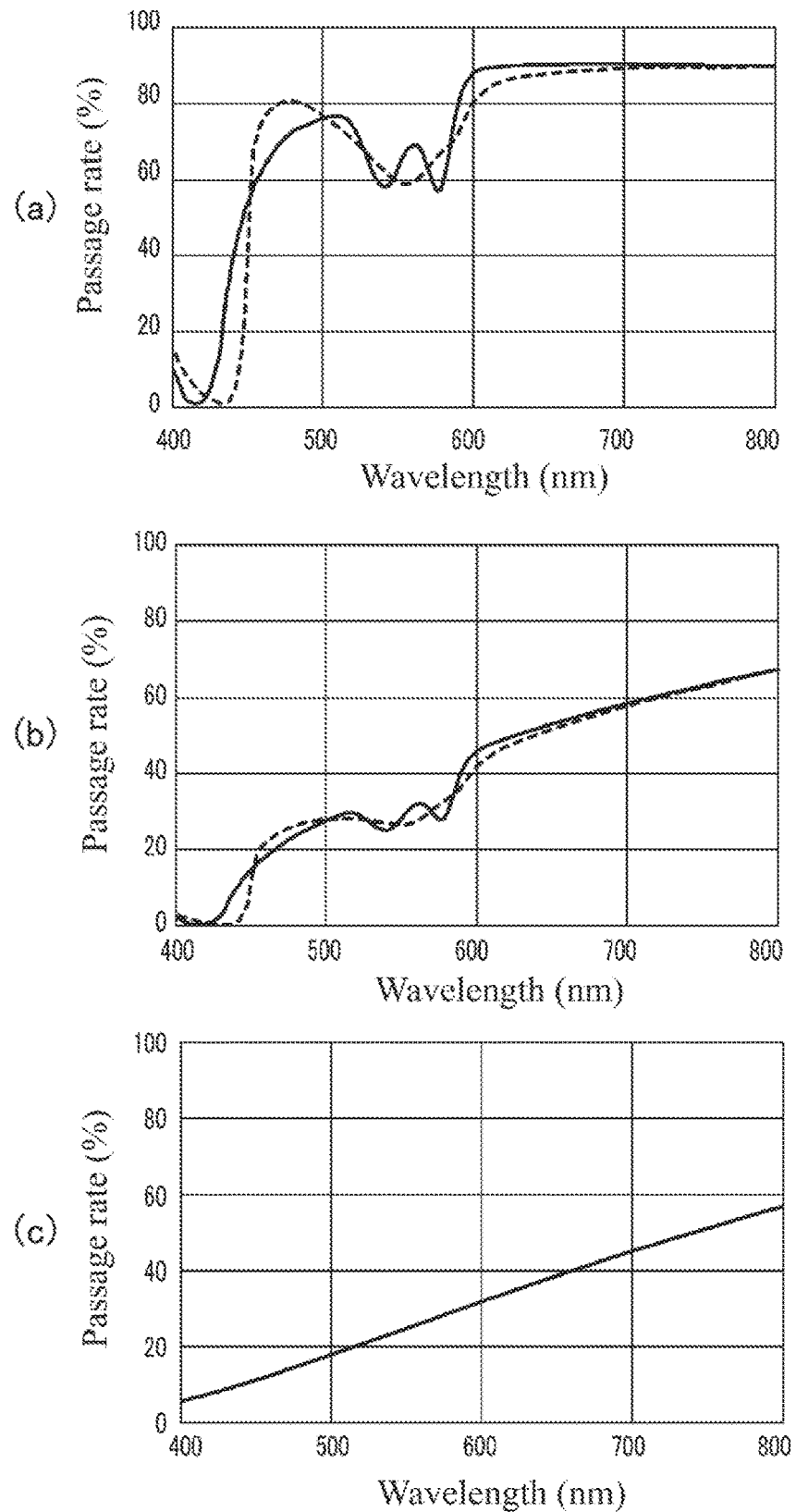
FIG. 2 shows simulation results for spectral characteristics (reflection spectrum) in the visible light range of a biological tissue.

Next, the influence of scattering on the spectral characteristics of biological tissue will be described. FIG. 2 shows spectral characteristics (reflection spectrums) in the visible light region of biological tissue obtained by simulation calculation, and shows the influence of light scattering on the spectral characteristics. In the graphs in FIG. 2, the horizontal axis indicates the wavelength (nm) of light, and the vertical axis indicates the passage rate (%) of light. The passage rate of light on the vertical axis corresponds to the reflectance of light by the biological tissue. The reflection spectrum of biological tissue such as a digestive track wall is known to be influenced by not only the absorption wavelength characteristics of the components that make up the biological tissue (specifically, the absorption spectrum characteristics of oxygenated hemoglobin and reduced hemoglobin), but also the wavelength characteristics of light scattering by biological tissue. FIG. 2(a) shows the reflection spectrum in the case where there is no scattering whatsoever. FIG. 2(c) shows the reflection spectrum in the case where there is no absorption whatsoever by hemoglobin. FIG. 2(b) shows the reflection spectrum in the case where the influence of scattering by the biological tissue (attenuation of light by scattering) and the influence of absorption by hemoglobin (attenuation of light by absorption) are approximately the same. Note that in FIGS. 2(a) and 2(b), the solid line indicates the reflection spectrum in the case where only oxygenated hemoglobin is included in the biological tissue, and the dashed line indicates the reflection spectrum in the case where only reduced hemoglobin is included in the biological tissue.

As shown in FIG. 2, the spectral characteristics of the biological tissue vary depending on the extent of scattering, and therefore biological information calculated based on the spectral characteristics of the biological tissue, such as the degree of oxygen saturation, may also change in value depending on the extent of scattering. In other words, if the biological tissue spectral characteristics (e.g., reflectance in the wavelength region W5) are used as-is to calculate the biological information, a calculation result that contains error arising from scattering will be obtained. In order to obtain a precise analysis result, it is necessary to correct the error arising from scattering.

Methods of correcting error arising from scattering include a method of correcting error after calculating biological information such as the degree of oxygen saturation based on biological tissue spectral characteristics, and a method of generating an intermediate parameter that is not dependent on scattering based on biological tissue spectral characteristics (removing the component that is dependent on scattering at the stage of generating the intermediate parameter), and then calculating biological information based on the correlation relationship between the intermediate parameter and the biological information. In the present disclosure, the latter method is used to acquire biological information that does not contain error arising from scattering. In order to realize this method, the inventors of the present disclosure performed intensive examination and found a parameter that has high sensitivity to (is highly correlated with) biological information that is to be acquired (specifically, the total hemoglobin amount and the degree of oxygen saturation, which are biological tissue feature amounts), and also has almost no sensitivity to scattering.

Figure 3:
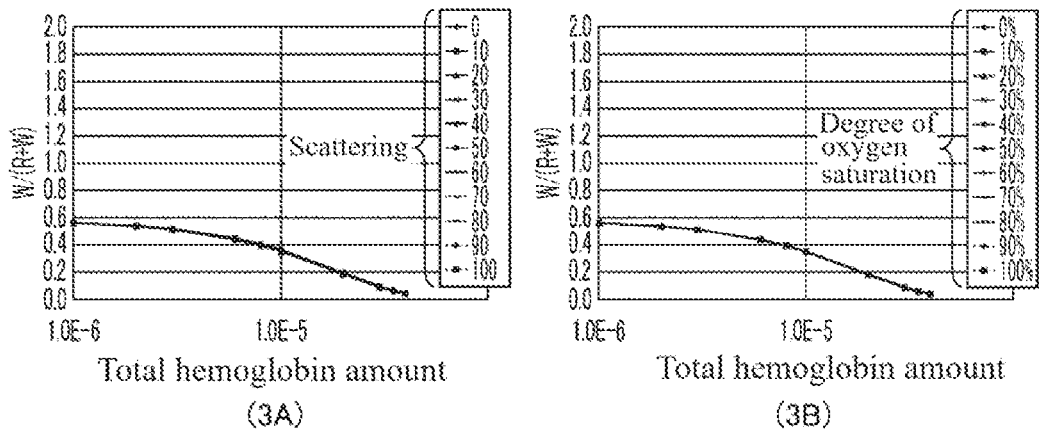
FIG. 3 includes graphs showing correlations between parameters and biological information.
Figure 4:
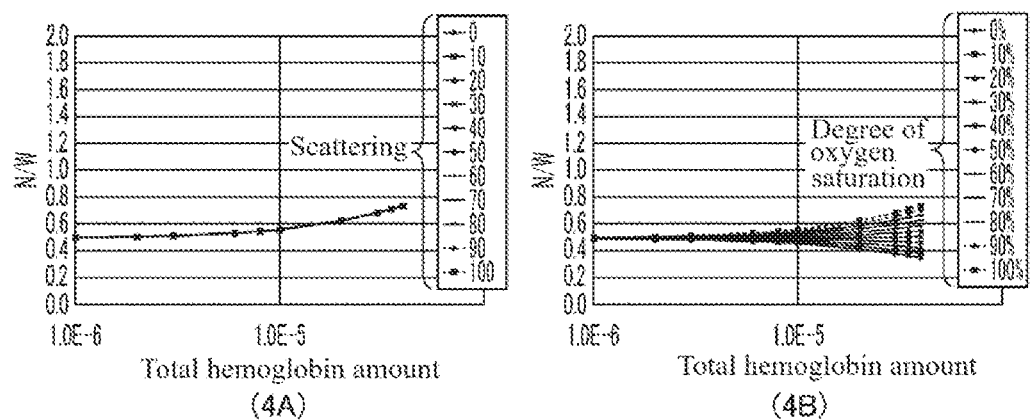
FIG. 4 includes graphs showing correlations between parameters and biological information.
Figure 5:
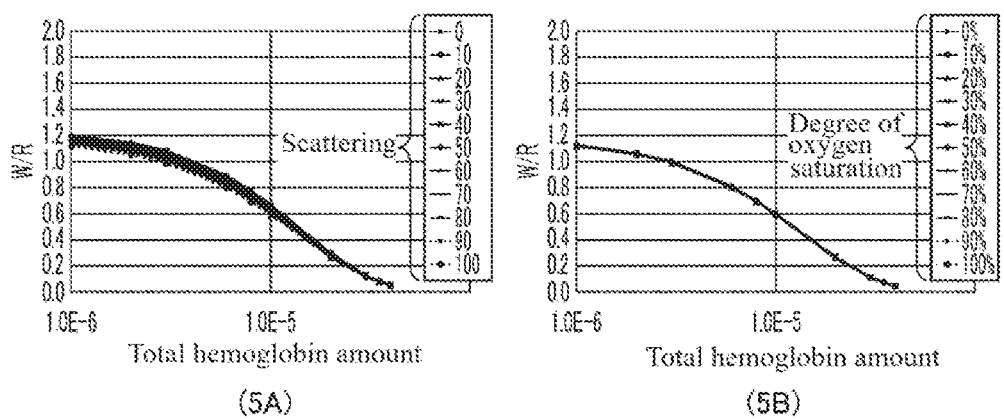
FIG. 5 includes graphs showing correlations between parameters and biological information.

FIGS. 3, 4, and 5 are graphs showing plots of simulation results of various parameters that can be acquired from endoscopic image data. The horizontal axis in the graphs indicates the total hemoglobin amount, and the vertical axis indicates parameter values.

Graphs (3A) and (3B) in FIG. 3 are graphs plotting simulation results for the parameter "W/(R+W)". The parameter "W/(R+W)" is the result of the pixel value W of G pixels (color pixels provided with a green G color filter) obtained by observation performed using illumination light in the W band being divided by the sum "R+W" of the pixel value R of R pixels (color pixels provided with a red R color filter) obtained by observation performed using illumination light in the WR band and the pixel value W of G pixels obtained by observation performed using illumination light in the W band. Note that as will be described later, the wavelength region W7 is included in a wavelength region in which G pixels of the image sensor have sensitivity. Also, the wavelength region WR is included in a wavelength region in which the R pixels of the image sensor have sensitivity.

Graphs (4A) and (4B) in FIG. 4 are graphs plotting simulation results for the parameter "N/W". The parameter "N/W" is the result of the pixel value N of G pixels obtained by observation performed using illumination light in the N band being divided by the pixel value W of G pixels obtained by observation performed using illumination light in the W band.

The graphs (3A) and (4A) in FIGS. 3 and 4 are graphs in which the degree of oxygen saturation is fixed at 100%, and the contribution of scattering (parameter indicating the intensity of scattering) is varied between 0 and 100 in units of 10 and plotted in an overlapped manner. Based on these graphs (3A) and (4A), it is possible to find out the degree of sensitivity of the parameters to scattering. The graphs (3B) and (4B) in FIGS. 3 and 4 are graphs in which the contribution of scattering is set to 0, and the degree of oxygen saturation is varied between 0 and 100% in units of 10% and plotted in an overlapped manner. Based on these graphs (3B) and (4B), it is possible to find out the degree of sensitivity of the parameters to the degree of oxygen saturation.

As shown in the graphs (3A) and (3B), the parameter "W/(R+W)" has sensitivity to the total hemoglobin amount, but has almost no sensitivity to scattering or the degree of oxygen saturation. For this reason, a value the total hemoglobin amount that is accurate and does not have dependency on scattering or the degree of oxygen saturation is obtained based the quantitative relationships between the total hemoglobin amount and the parameter "W/(R+W)" shown in the graphs (3A) and (3B).

Also, as shown in the graphs (4A) and (4B), the parameter "N/W" has high sensitivity to the degree of oxygen saturation, but has almost no sensitivity to scattering. For this reason, if the total hemoglobin amount is known, the value of the degree of oxygen saturation can be uniquely determined based on the value of the parameter "N/W" according to the graph (4B). Specifically, if the plotted point in the graph (4B) that most closely conforms to the numerical value pair of the value of the total hemoglobin amount and the value of the parameter "N/W" obtained from the pixel values is selected, the degree of oxygen saturation of the subject appearing at that pixel is obtained.

As described above, by performing simple calculation using the relationships shown in the graphs (3A) and (3B) and the relationship shown in the graph (4B), it is possible to obtain accurate values for the total hemoglobin amount and the degree of oxygen saturation that contain almost no error arising from scattering.

Note that the parameter for obtaining the total hemoglobin amount is not limited to "W/(R+W)". For example the parameter for obtaining the total hemoglobin amount may be "W/R". Graphs (5A) and (5B) in FIG. 5 are graphs plotting simulation results for the parameter "W/R". The parameter "W/R" is the result of the pixel value W of G pixels obtained by observation performed using illumination light in the W band being divided by the pixel value R of R pixels obtained by observation performed using illumination light in the WR band.

The graph (5A) in FIG. 5 is a graph in which the degree of oxygen saturation is fixed at 100%, and the contribution of scattering (parameter indicating the intensity of scattering) is varied between 0 and 100 in units of 10 and plotted in an overlapped manner. Based on this graph (5A), it is possible to find out the degree of sensitivity of the parameter "W/R" to scattering. The graphs (5B) in FIG. 5 is a graph in which the contribution of scattering is set to 0, and the degree of oxygen saturation is varied between 0 and 100% in units of 10% and plotted in an overlapped manner. Based on this graph (5B), it is possible to find out the degree of sensitivity of the parameter "W/R" to the degree of oxygen saturation.

As shown in the graphs (5A) and (5B), the parameter "W/R" has sensitivity to the total hemoglobin amount, but has almost no sensitivity to scattering or the degree of oxygen saturation. For this reason, it is understood here that the value of the total hemoglobin amount is uniquely determined by the value of the parameter "W/R".

Also, the parameter for obtaining the total hemoglobin amount may be the result of multiplying the pixel value W by a constant C, as in "W/(R+C×W)" for example. Furthermore, the denominator of the parameter for obtaining the total hemoglobin amount may include "B". "B" is the pixel value of B pixels (color pixels provided with the blue B color filter) obtained by observation performed using illumination light in the W2 band. For this reason, the parameter for obtaining the total hemoglobin amount can be expressed as "W/(C1×R+C2×W+C3×B)" for example. Here, C1, C2, and C3 are constants. These constants C, C1, C2, and C3 are appropriately adjusted according to the characteristics of the RGB color filters provided on the color pixels. Adjusting the constants C, C1, C2, and C3 makes it possible to obtain a parameter that has sensitivity to the total hemoglobin amount, but has almost no sensitivity to scattering and the degree of oxygen saturation.

Also, the numerator of the parameter for obtaining the total hemoglobin amount may be "N" instead of "W". In this case, the parameter for obtaining the total hemoglobin amount can be expressed as "N/(C1×R+C2×W+C3×B)" for example. The constants C1, C2, and C3 are appropriately adjusted according to the characteristics of the RGB color filters provided on the color pixels.

Configuration of Endoscope Device

Figure 6:
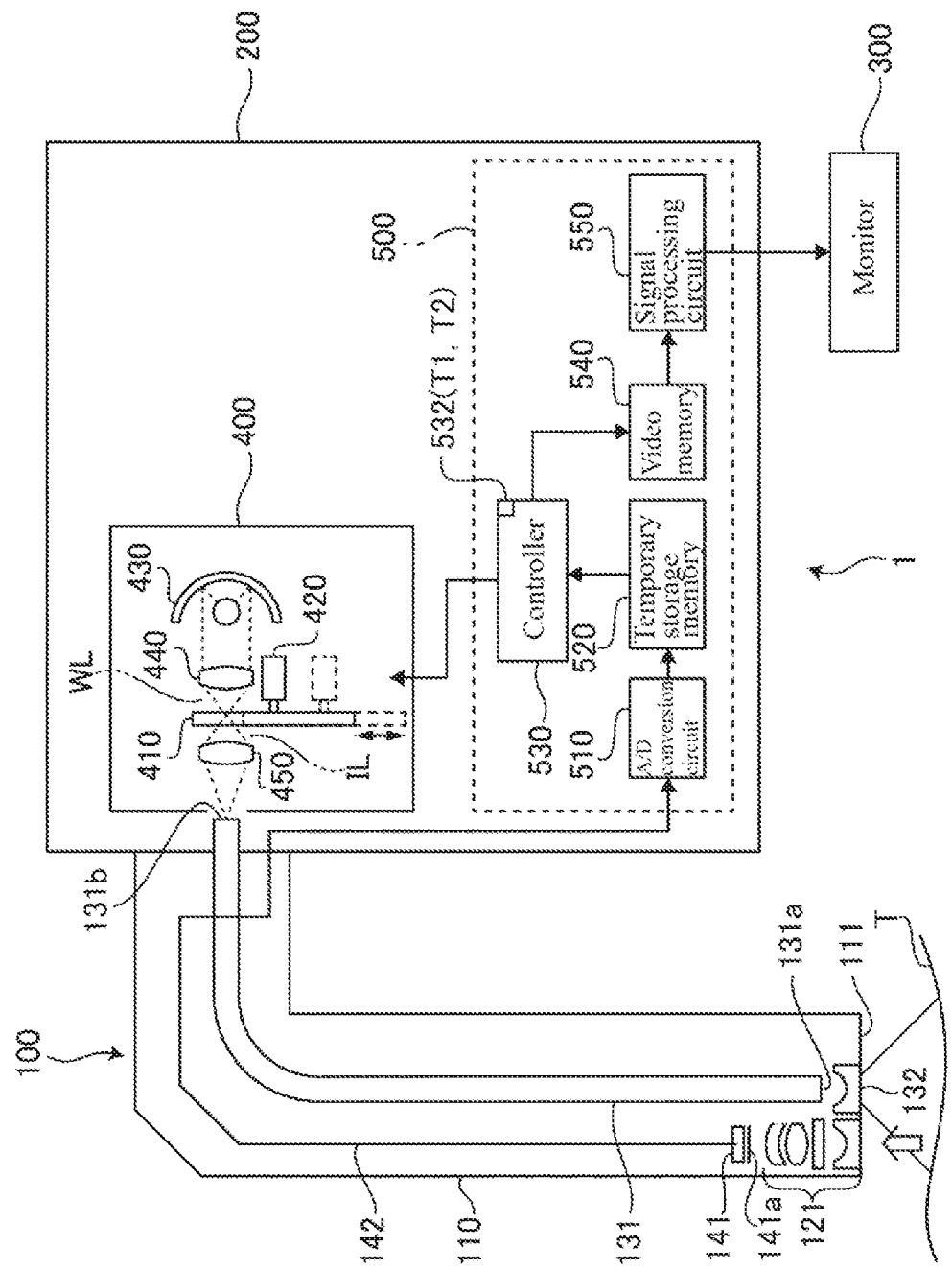
FIG. 6 is a block diagram of an endoscope device according to an embodiment of the present disclosure.

FIG. 6 is a block diagram of an endoscope device 1 according to an embodiment of the present disclosure. The endoscope device 1 of the present embodiment includes an electronic endoscope 100, a processor 200, and a monitor 300. The electronic endoscope 100 and the monitor 300 are detachably connected to the processor 200. Also, a light source unit 400 and an image processing unit 500 are built into the processor 200.

The electronic endoscope 100 has an insertion tube 110 for insertion into the subject's body. The electronic endoscope 100 is internally provided with a light guide 131 that extends over approximately the entire length thereof. One end portion (distal end portion 131a) of the light guide 181 is arranged in the distal end portion of the insertion tube 110 (insertion tube distal end portion 111), and the other end portion (base end portion 131b) of the light guide 131 is connected to the processor 200. The processor 200 includes a light source unit 400 that includes a light source 430 or the like for generating high-intensity white light WL, such as a xenon lamp, and the illumination light IL generated by the light source unit 400 enters the base end portion 131b of the light guide 131. Light that enters the base end portion 131b of the light guide 131, passes through the light guide 131 and is guided to the distal end portion 131a thereof, and is then emitted from the distal end portion 131a. A light distribution lens 132 arranged opposing the distal end portion 131a of the light guide 131 is provided at the insertion tube distal end portion 111 of the electronic endoscope 100. Illumination light IL emitted from the distal end portion 131a of the light guide 131 passes through the light distribution lens 132 and illuminates biological tissue T in the vicinity of the insertion tube distal end portion 111.

Also, the insertion tube distal end portion 111 is provided with an objective optical system 121 and an image sensor 141. Part of the light reflected or scattered by the surface of the biological tissue T (returning light) enters the objective optical system 121, is condensed, and forms an image on the light receiving surface of the image sensor 141. The image sensor 141 of the present embodiment is a CCD (Charge Coupled Device) image sensor for color image capturing, and includes a color filter 141a on its light receiving surface. Another type of image sensor such as a CMOS (Complementary Metal Oxide Semiconductor) image sensor may be used as the image sensor 141.

Figure 7:
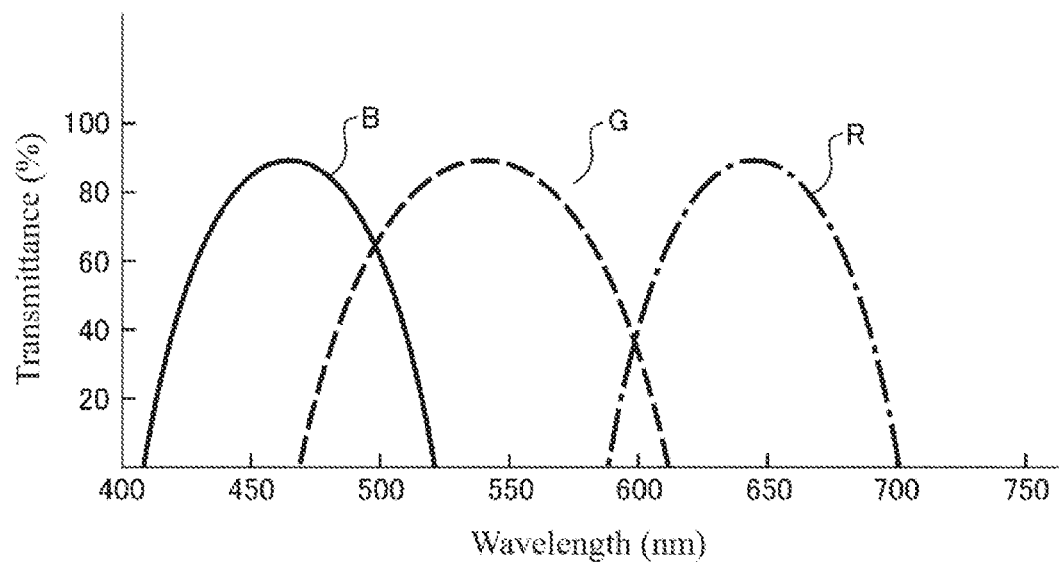
FIG. 7 shows transmission characteristics of a color filter of an image sensor according to the embodiment of the present disclosure.

The color filter 141a includes an array of color filters that allow red light to pass, G color filters that allow green light to pass, and B color filters that allow blue light to pass, and is a so-called on-chip filter that is formed directly on the light receiving element of the image sensor 141. FIG. 7 shows the transmission characteristics of the R, G, and B color filters. In FIG. 7, the horizontal axis indicates the wavelength (nm), and the vertical axis indicates the transmittance (%). The R color filters of the present embodiment are filters that allow light with a wavelength longer than approximately 570 nm to pass (be transmitted), the G color filters are filters that allow light with a wavelength of approximately 470 nm to 620 nm to pass (be transmitted), and the B color filters are filters that allow light with a wavelength shorter than approximately 530 nm to pass (be transmitted).

The image sensor 141 is controlled to operate in synchronization with a signal processing circuit 550 that will be described later, and outputs an imaging signal that corresponds to a subject image formed on the light receiving surface, at a predetermined frame rate (e.g., at intervals of 1/30 second). The imaging signal output from the image sensor 141 is sent to the image processing unit 500 of the processor 200 via a cable 142.

The image processing unit 500 includes an A/D conversion circuit 510, a temporary storage memory 520, a controller 530, a video memory 540, and a signal processing circuit 550. The A/D conversion circuit 510 performs A/D conversion on an imaging signal received from the image sensor 141 of the electronic endoscope 100 via the cable 142, and outputs digital image data. The digital image data output from the A/D conversion circuit 510 is sent to and stored in the temporary storage memory 520. This digital image data includes R digital image data obtained by the light receiving elements on which the R color filters are mounted, G digital image data obtained by the light receiving elements on which the G color filters are mounted, and B digital image data obtained by the light receiving elements on which the B color filters are mounted.

The controller 530 processes one or more pieces of digital image data stored in the temporary storage memory 520 to generate screen data for display on the monitor 300, and sends the screen data to the video memory 540. The signal processing circuit 550 generates a video signal in a predetermined format a format compliant with NTSC standards or DVI standards) based on screen data that is stored in the video memory 540, and outputs the video signal. The video signal output from the signal processing circuit 550 is received by the monitor 300. As a result, an endoscopic image of the biological tissue T or the like captured by the electronic endoscope 100 is then displayed on the monitor 300.

In this way, the processor 200 includes both functionality as a video processor that processes imaging signals output from the image sensor 141 of the electronic endoscope 100, and functionality as a light source device that supplies illumination light IL, which is for illuminating the biological tissue T that is the imaging subject, to the light guide 131 of the electronic endoscope 100.

Besides the above-described light source 430, the light source unit 400 also includes a condensing lens 440, a rotating filter 410, a filter control unit 420, and a condensing lens 450. Approximately parallel white light WL that exits the light source 430 is condensed by the condensing lens 440, passes through the rotating filter 410, is then again condensed by the condensing lens 450, and then enters the base end portion 131b of the light guide 131. Note that the rotating filter 410 can be moved between an application position on the optical path of the white light WL and a retracted position off the optical path by a moving means (not shown) such as a linear guideway.

Note that the configuration of the light source unit 400 is not limited to the configuration shown FIG. 6. For example, a lamp that generates convergent light may be employed as the light source 430. In this case, a configuration may be employed in which, for example, white light WL is condensed before reaching the condensing lens 440, and then caused to enter the condensing lens 440 as diffused light.

Also, a configuration may be employed in which the condensing lens 440 is not used, and approximately parallel light generated by the light source 430 is caused to directly enter the rotating filter 410.

Also, in the case of using a lamp that generates convergent light, a configuration may be employed in which a collimator lens is used instead of the condensing lens 440 in order to cause white light WL that is in an approximately parallel state to enter the rotating filter 410. For example, in the case of using an interference type of optical filter such as a dielectric multilayer filter as the rotating filter 410, by causing approximately parallel white light WL to enter the rotating filter 410, the angle of incidence of the white light WL on the optical filter can be made uniform, thus making it possible to obtain more favorable filter characteristics.

Also, a lamp that generates diverging light may be applied as the light source 430. In this case as well, a configuration can be employed in which a collimator lens is used instead of the condensing lens 440 in order to cause approximately parallel white light WL to enter the rotating filter 410.

The rotating filter 410 is a disc-type optical unit that includes multiple optical filters, and is configured such that the pass wavelength region is switched according to the rotation angle. The rotation angle of the rotating filter 410 is controlled by the filter control unit 420, which is connected to the controller 530. The controller 530 controls the rotation angle of the rotating filter 410 via the filter control unit 420, thus switching the spectrum of illumination light IL that passes through the rotating filter 410 and is supplied to the light guide 131.

Figure 8:
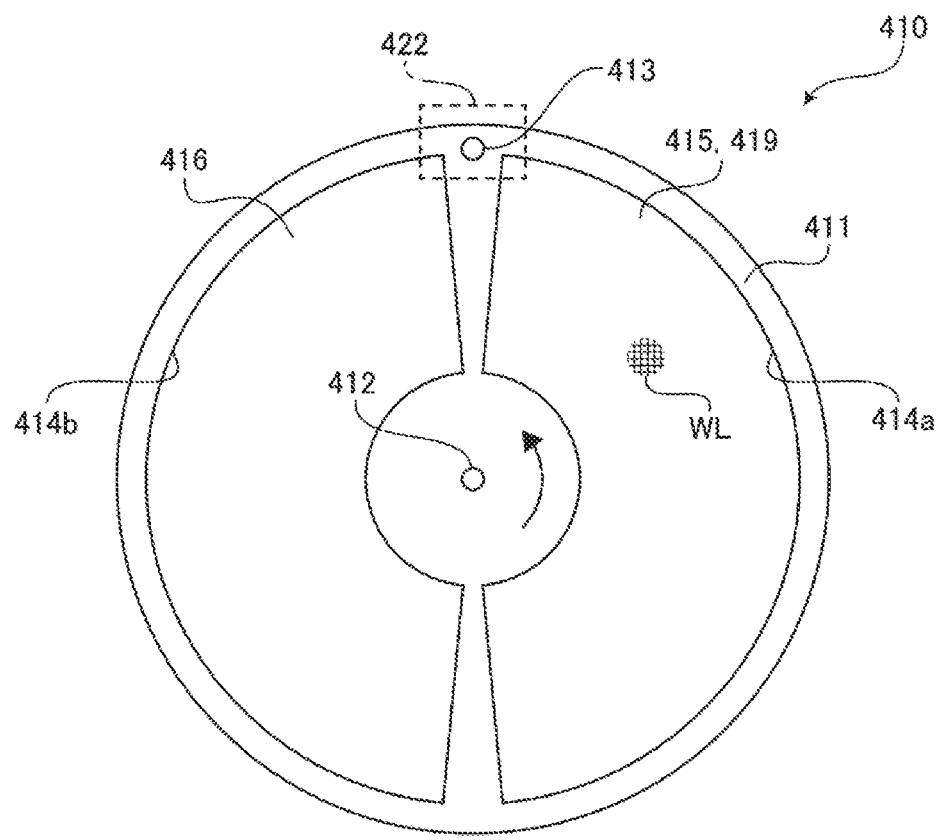
FIG. 8 is an external view of a rotating filter according to the embodiment of the present disclosure.

FIG. 8 is an external view (front view) of the rotating filter 410. The rotating filter 410 includes an approximately disc-shaped frame 411 and two fan-shaped optical filters 415 and 416. Two fan-shaped windows 414a and 414b are formed with equal gaps therebetween around the central axis of the frame 411, and the optical filters 415 and 416 are respectively fitted into the windows 414a and 414b. The angular ranges of the optical filters 415 and 416 about the central axis of the frame 411 are approximately 180°. Note that the optical filters of the present embodiment are both dielectric multilayer filters, but another type of optical filter (e.g., an absorption optical filter or an etalon filter that uses a dielectric multilayer film as a reflection film) may be used.

Also, a boss hole 412 is formed on the central axis of the frame 411. An output shaft of a servo motor (not shown) of the filter control unit 420 is inserted in and fixed to the boss hole 412, and the rotating filter 410 rotates along with the output shaft of the servo motor.

Although the state where white light WL enters the optical filter 415 is shown in FIG. 8, when the rotating filter 410 rotates in the direction indicated by the arrow, the optical filter that the white light WL enters switches between the optical filters 415 and 416, and thus the spectrum of light IL that passes through the rotating filter 410 switches successively. Hereinafter, the illumination light IL that passes through the optical filter 415 will also be called first special light, and the illumination light IL that passes through the optical filter 416 will also be called second special light.

FIGS. 9(a) and 9(b) respectively show the transmission spectrums of the optical filters 415 and 416. In FIGS. 9(a) and 9(b), the horizontal axis indicates the wavelength (nm), and the vertical axis indicates the transmittance (%).

The optical filter 415 has a transmission characteristic of allowing light in the wavelength region W2, the wavelength region W7 (W band), and the wavelength region WR shown in FIG. 1 to pass (be transmitted) with low loss. Specifically, the optical filter 415 has a transmission characteristic of allowing the passage of light in a wavelength region of wavelengths less than 502 nm, a wavelength region of wavelengths greater than or equal to 528 nm and less than 584 nm, and a wavelength region of wavelengths greater than or equal to 620 nm. Also, the optical filter 415 blocks light in a wavelength region of wavelengths greater than or equal to 502 nm and less than 528 nm, and a wavelength region of wavelengths greater than or equal to 584 nm and less than 620 nm. Note that in the wavelength region of wavelengths less than 502 nm, it is sufficient that the optical filter 415 allows the transmission of light in the wavelength region W2, and there are no particular limitations on the lower limit of the wavelength region of light that passes through the optical filter 415. Also, in the wavelength region of wavelengths greater than or equal to 620 nm, it is sufficient that the optical filter 415 allows the transmission of light in the wavelength region WR, and there are no particular limitations on the upper limit of the wavelength region of light that passes through the optical filter 415.

The optical filter 416 has a transmission characteristic of allowing light in the wavelength region W5 (N band) shown in FIG. 1 to pass (be transmitted) with low loss. Specifically, the optical filter 416 has a transmission characteristic of allowing the passage of light in a wavelength region of wavelengths greater than or equal to 546 nm and less than 570 nm. Also, the optical filter 415 blocks light in wavelength regions outside the wavelength region W5.

Moreover, the wavelength region W2, the wavelength region W7 (W band), and the wavelength region WR, which are the pass wavelength regions of the optical filter 415, are included in the pass wavelength regions of the B color filter, the G color filter, and the R color filter of the color filter 141a (FIG. 7). Accordingly, B digital image data, G digital image data, and R digital image data are obtained from the components in the wavelength region W2, the wavelength region W7, and the wavelength region WR in the subject image formed by the first special light that passes through the optical filter 415.

Also, the wavelength region W5 (N band), which is the pass wavelength region of the optical filter 416, is included in the pass wavelength region of the G color filter of the color filter 141a (FIG. 7). Accordingly, G digital image data is obtained from the subject image formed by the second special light that passes through the optical filter 416.

Also, a light attenuation filter (ND filter) 419 is attached over the optical filter 415 in the window 414a. The light attenuation filter 419 has no wavelength dependency over the entire visible light range, and merely reduces the quantity of light with no change in the spectrum of illumination light IL. By using the light attenuation filter 419, the quantity of illumination light IL that passes through the optical filter 415 and the light attenuation filter 419 is adjusted to approximately the same as the quantity of illumination light IL that passes through the optical filter 416. According regardless of whether illumination light IL that passed through the optical filter 415 or the optical filter 416 is used, it is possible to capture an image with the same exposure time and appropriate exposure.

In the present embodiment, a fine metal mesh is used as the light attenuation filter 419. Besides a metal mesh, another type of light attenuation filter such as a slit or half mirror type may be used. Also, a configuration is possible in which a light attenuation filter is not used, and the transmittances of the optical filters 415 and 416 themselves are adjusted. Furthermore, a configuration is possible in which a light attenuation filter is not used, and the exposure time is adjusted for each optical filter that is used.

A through-hole 413 is formed in the peripheral edge portion of the frame 411. The through-hole 413 is formed at the same position (phase) as the boundary portion between the window 414a and the window 414b in the rotation direction of the frame 411. A photo interrupter 422 for detecting the through-hole 413 is arranged in the periphery of the frame 411 so as to surround a portion of the peripheral edge portion of the frame 411. The photo interrupter 422 is connected to the filter control unit 420.

The endoscope device 1 of the present embodiment has two operating modes, namely a normal observation mode and a spectral analysis mode. In the normal observation mode, the rotating filter 410 is moved to a retracted position. For this reason, the white light WL emitted from the light source 430 irradiates the biological tissue without limitation of the wavelength band by the optical filters 415 and 416. Then, the image processing unit 500 performs predetermined image processing such as demosaicing on digital image data obtained by the image sensor 141, converts the processed digital image data into a video signal, and displays the video signal on the screen of the monitor 300. Accordingly, a color captured image of the biological tissue can be captured using while illumination light. Note that in the normal observation mode, a filter (not shown) may be used to remove a component outside the visible light range, such as a component in the infrared range or the ultraviolet range, before the white light WL is emitted onto the biological tissue.

In the spectral analysis mode, the rotating filter 410 is moved to an application position. The controller 530 controls the filter control unit 420 so as to rotationally drive the rotating filter 410 at a constant rotational frequency, and successively capture images of the biological tissue T illuminated with the first special light and the second special light that respectively pass through the optical filters 415 and 416. Based on digital image data acquired using the first special light and the second special light, the image processing unit 500 generates color image data for the biological tissue and analysis image data that shows the distribution of a biological substance in the biological tissue. Then image processing unit 500 then generates screen data including the color image and the analysis image side-by-side based on the color image data and the analysis image data, converts the generated image data into a video signal, and displays the video signal on the monitor 300.

In the spectroscopic analysis mode, the filter control unit 420 detects the phase of rotation of the rotating filter 410 based on the timing of detection of the through-hole 413 by the photo interrupter 422, compares the detected phase with the phase of a timing signal supplied by the controller 530, and adjusts the phase of rotation of the rotating filter 410. The timing signal from the controller 530 is synchronized with the drive signal for the image sensor 141. Accordingly, the rotating filter 410 is driven to rotate at a substantially constant rotational frequency in synchronization with the driving of the image sensor 141. Specifically, the rotation of the rotating filter 410 is controlled such that the optical filter that white light WL enters is switched between the optical filter 415 and the optical filter 416 each time one image captured by the image sensor 141 (i.e., each frame).

Figure 10:
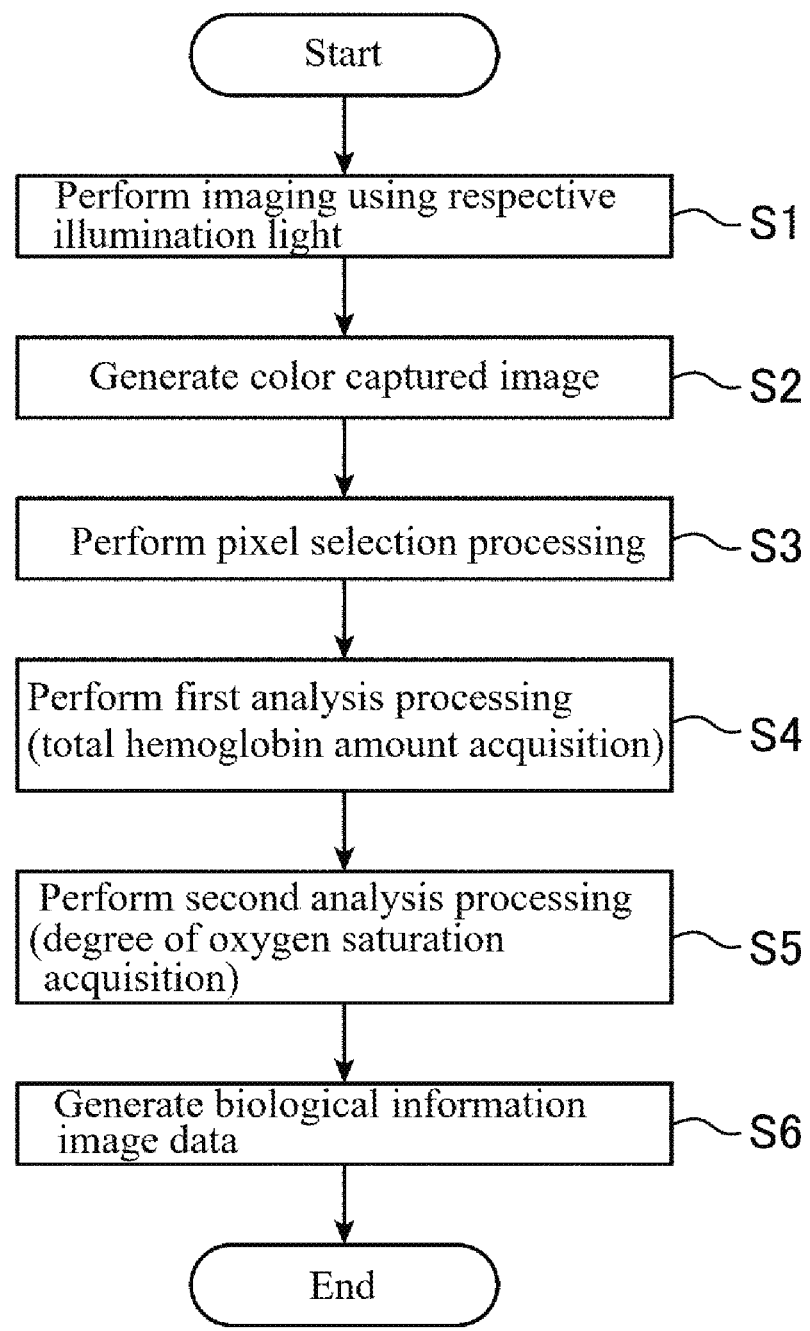
FIG. 10 is a flowchart illustrating spectral analysis processing according to the embodiment of the present disclosure.

Next, spectral analysis processing executed in the spectral analysis mode will be described. FIG. 10 is a flowchart showing a procedure of spectral analysis processing.

In processing step S1, images of the biological tissue are captured using the illumination light IL (first special light and second special light) that passes through the optical filters 415 and 416. Specifically, using the first special light that passes through the optical filter 415, R digital image data R(x,y), G digital image data W(x,y), and B digital image data B(x,y) are stored in the internal memory 532 of the controller 530. Also, using the second special light that passes through the optical filter 416, G digital image data N(x,y) is stored in the internal memory 532.

In processing step S2, color captured image data for the biological tissue is generated. The color captured image data is generated using the R digital image data R(x,y), the G digital image data W(x,y), and the B digital image data B(x,y). The pieces of image data R(x,y), W(x,y), and B(x,y) respectively express the red, green, and blue components of the subject image. For this reason, full-color captured image data for the biological tissue can be generated using these pieces of image data R(x,y), W(x,y), and B(x,y). Note that the color captured image data may be generated using G digital image data N(x,y), which expresses the green component of the subject image, instead of the G digital image data W(x,y).

In processing step S3, pixel selection processing is performed for selecting pixels that are to be subjected to subsequent analysis processing (processing steps S4 to S6), using the R digital image data R (x,y), the G digital image data G (x,y), and the B digital image data B (x,y) acquired in processing step S1.

In the biological tissue that is the subject, at locations in the image data where blood is not included, or locations where the biological tissue color is dominantly influenced by a substance other than hemoglobin, even if the degree of oxygen saturation or blood flow is calculated based on color information obtained from the image data, a meaningful value is not obtained, but rather is simply noise. If such obtained noise is presented to a physician, it will not only be a hindrance to an appropriate diagnosis, but also have the harmful effect of placing an unnecessary burden on the image processing unit 500 and reducing the processing speed. In view of this, the analysis processing of the present embodiment is configured such that pixels suited to analysis processing pixels recording the spectroscopic features of blood) are selected, and analysis processing is performed on only the selected pixels.

In pixel selection processing S3, only pixels that satisfy all of the conditions of Expressions 5, 6, and 7 below are selected as target pixels for analysis processing.

$B(x,y)/G(x,y) > a1$ \hfill Expression 5

$R(x,y)/G(x,y) > a2$ \hfill Expression 6

$R(x,y)/B(x,y) > a3$ \hfill Expression 7

Here, a1, a2, and a3 are positive constants.

The above three conditional expressions are set based on the magnitude relationship of [G component value<B component value<R component value] in the transmission spectrum of blood. Note that pixel selection processing S3 may be performed using only one or two of the above three conditional expressions (e.g., using only Expressions 6 and/or 7 when focusing on the color red which is specific to blood).

In processing step S4, processing for acquiring the total hemoglobin amount of the biological tissue is performed. The internal memory 532 of the controller 530 holds a numerical value table T1 (or function) that expresses the quantitative relationship between the total hemoglobin amount tHb and the parameter W(R+W) shown in the graphs (3A) and (3B) in FIG. 3. In processing step S4, this numerical value table T1 is used to acquire the value of the total hemoglobin amount tHb based on the G digital image data W(x,y) and the R digital image data R(x,y) acquired in processing step S1.

Specifically, first, the parameter W/(R+W)(x,y) for each pixel (x,y) is calculated using Expression 8.

$W(R+W)(x,y) = W(x,y)/(R(x,y)+W(x,y))$ \hfill Expression 8

Next, the numerical value table T1 is referenced to read out and acquire the value of the total hemoglobin amount tHb(x,y) that corresponds to the value of the parameter W/(R+G)(x,y) calculated using Expression 8.

The quantitative relationship in the numerical value table T1 (and the later-described numerical value table T2) held in the internal memory 532 is obtained in advance by theoretical calculation or experimentation. Note that although a complete one-to-one correspondence does not exist for the value of the total hemoglobin amount tHb and the value of the parameter W/(R+W) in the graphs (3A) and (3B), a representative one-to-one quantitative relationship (e.g., average value or mean value) is held in the numerical value table T1 for the total hemoglobin amount tHb and the parameter W/(R+W). For this reason, the total hemoglobin amount tHb can be uniquely determined based on the value of the parameter W/(R+W) using the numerical value table T1.

Note that as described in section "Spectral characteristics of biological tissue and principle of calculation of biological information" above, in the present embodiment, the parameter for determining the total hemoglobin amount tHb is not limited to W/(R+W). For example, W/(C1×R+C2×W+C3×B) may be used as the parameter for determining the total hemoglobin amount tHb.

In processing step S5, processing for acquiring the degree of oxygen saturation of the biological tissue is performed. The internal memory 532 of the controller 530 holds a numerical value table T2 (or function) that expresses the quantitative relationship between the total hemoglobin amount tHb, the parameter N/W, and the degree of oxygen saturation Sat shown in the graph (4B) in FIG. 4. Three numerical values (called a "numerical value set"), namely the total hemoglobin amount tHb, the parameter N/W, and the degree of oxygen saturation Sat, are registered in association with each other in the numerical value table T2. In processing step S5, this numerical value table T2 is used to acquire the value of the degree of oxygen saturation Sat(x,y) for each pixel based on the G digital image data W(x,y) and N(x,y) acquired in processing step S1 and the value of the total hemoglobin amount tHb(x,y) acquired in processing step S4.

Specifically, first, the parameter N/W(x,y) for each pixel (x,y) is calculated using Expression 9.

$$N/W(x,y)=N(x,y)/W(x,y) \qquad \text{Expression 9}$$

Next, for each pixel (x,y), the numerical value table T2 is referenced to extract the numerical value set that is closest to the value of the total hemoglobin amount tHb(x,y) acquired in processing step S4 and the value of the parameter N/W(x,y) calculated using Expression 8, and then the value of the degree of oxygen saturation Sat in the extracted numerical value set is read out and acquired as the value of the degree of oxygen saturation Sat(x,y) at that pixel (x,y).

In processing step S6, processing for generating analysis image data is performed. The internal memory 532 of the controller 530 stores numerical value table (or function) that expresses the relationship between the degree of oxygen saturation Sat(x,y) and display colors (pixel values). The controller 530 then references this numerical value table (or function), and generates biological information image data using pixel values that indicate the display colors corresponding to the degree of oxygen saturation Sat(x,y) obtained in processing step S5. Analysis image data that expresses a degree of oxygen saturation distribution is thus generated.

Figure 11:
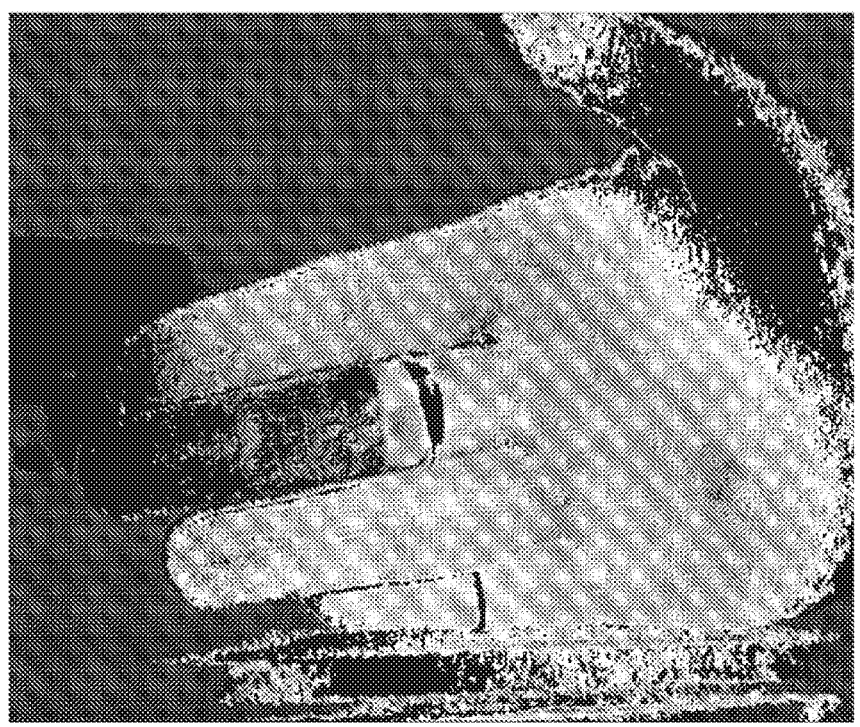
FIG. 11 shows an example of a display of analysis image data according to the embodiment of the present disclosure.
Figure 11:
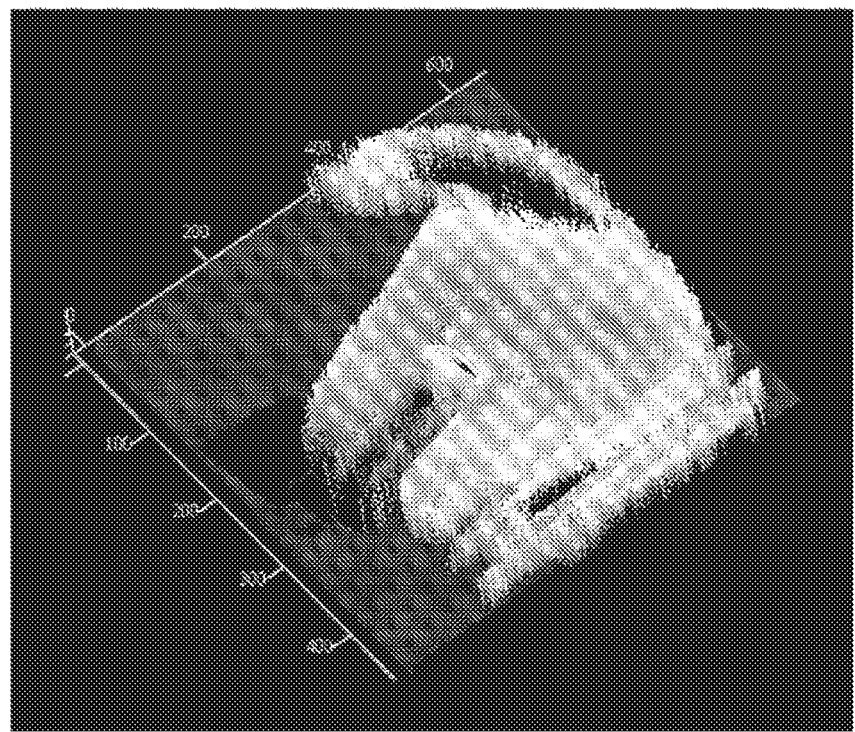

FIG. 11 shows an example of the display of analysis image data generated by the controller 530. FIG. 11(a) is an example of the display of analysis image data (two-dimensional display) showing the degree of oxygen saturation distribution generated by processing step S6 described above. Also, FIG. 11(b) is an example of the display of analysis data (three-dimensional display) generated in a three-dimensional graph format in which the degree of oxygen saturation is the vertical axis. Note that FIG. 11 shows the observation of a right hand in the state where an elastic band constricts the vicinity of the proximal interphalangeal joint of the middle finger. On the distal side of the constricted site of the right middle finger, the flow of blood is inhibited by the constriction, and therefore it is seen that the degree of oxygen saturation is low.

The controller 530 then uses the color captured image data generated in processing step S2 and the analysis image data generated in processing step S6 to generate screen data in which the color captured image and the analysis image are displayed side-by-side in one screen, and stores the screen data in the video memory 540. Note that in accordance with a user operation, the controller 530 can generate various types of display screens, such as a display screen that displays only the analysis image, a display screen that displays only the color captured image, or a display screen that displays supplementary information such as patient ID information and observation conditions in a superimposed manner on the analysis image and/or the color captured image.

Malignant tumor tissue has a higher total hemoglobin amount than normal tissue due to angiogenesis, and also exhibits remarkable oxygen metabolism, and therefore it is known that the degree of oxygen saturation is lower than that of normal tissue. In view of this, the controller 530 can perform processing to extract the pixels for which the total hemoglobin amount acquired in processing step S4 is greater than a predetermined reference value (first reference value), and for which the degree of oxygen saturation acquired in processing step S5 is less than a predetermined reference value (second reference value), perform enhanced display processing on corresponding pixels of normal observation image data for example to generate enhanced lesion site image data, and display the enhanced lesion site image on the monitor 300 along with the normal observation image and/or the degree of oxygen saturation distribution image (or on its own).

Examples of enhanced display processing include processing for increasing the pixel values of corresponding pixels, processing for changing the hue (e.g., processing for increasing the redness by increasing the R component, or processing for rotating the hue by a predetermined angle), and processing for flashing corresponding pixels (or periodically changing the hue).

Also, a configuration is possible in which, instead of generating enhanced lesion site image data, the controller 530 calculates an indicator Z(x,y) that indicates the degree of suspicion of a malignant tumor based on the deviation of the degree of oxygen saturation Sat(x,y) from an average value and the deviation of the total hemoglobin amount tHb(x,y) from an average value, and generate image data in which the pixel values are the indicator Z (malignancy suspicion image data).

Also, in processing step S6, the controller 530 may generate analysis image data that shows a total hemoglobin amount distribution. Alternatively, the controller 530 may generate both analysis image data that shows a total hemoglobin amount distribution, and analysis image data that shows a degree of oxygen saturation distribution.

In this way, according to the present embodiment, by setting the operating mode of the endoscope device 1 to the spectral analysis mode, it is possible to obtain the total hemoglobin amount and the degree of oxygen saturation of a biological tissue while suppressing error caused by scattering.

Also, according to the present embodiment, in the spectral analysis mode, it is possible to obtain a color captured image of the biological tissue at the same time as obtaining biological information such as the total hemoglobin amount and the degree of oxygen saturation.

Also, with the endoscope device disclosed in Patent Document 1, in the case of calculating an indicator that indicates the total hemoglobin amount and an indicator that indicates the degree of oxygen saturation, the frame rate of color captured images decreases to ¼. In contrast, in the present embodiment, if the operating mode of the endoscope device 1 is set to the spectral analysis mode, the optical filter 415 and the optical filter 416 are alternatingly inserted into the light path of the white light WL. Accordingly, images of the biological tissue are alternatingly captured using the first special light and the second special light. For this reason, the frame rate of color captured images of the biological tissue obtained in the spectral analysis mode is half the frame rate of color captured images in the normal observation mode. According to the present embodiment, it is therefore possible to obtain biological information while suppressing a decrease in the frame rate in comparison with the Patent Document 1.

Although an embodiment of the present disclosure and a specific working of the embodiment have been described above, the present disclosure is not limited to the above configurations, and various modifications can be made within the scope of the technical idea of the present disclosure.

Figure 9:
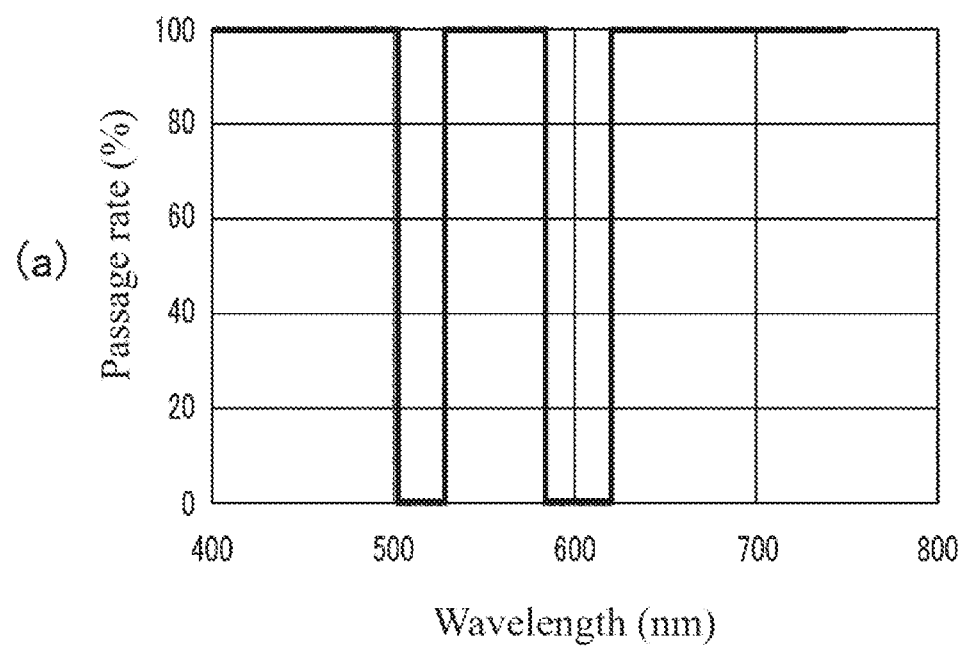
FIG. 9 shows transmission spectrums of optical filters according to the embodiment of the present disclosure.
Figure 9:
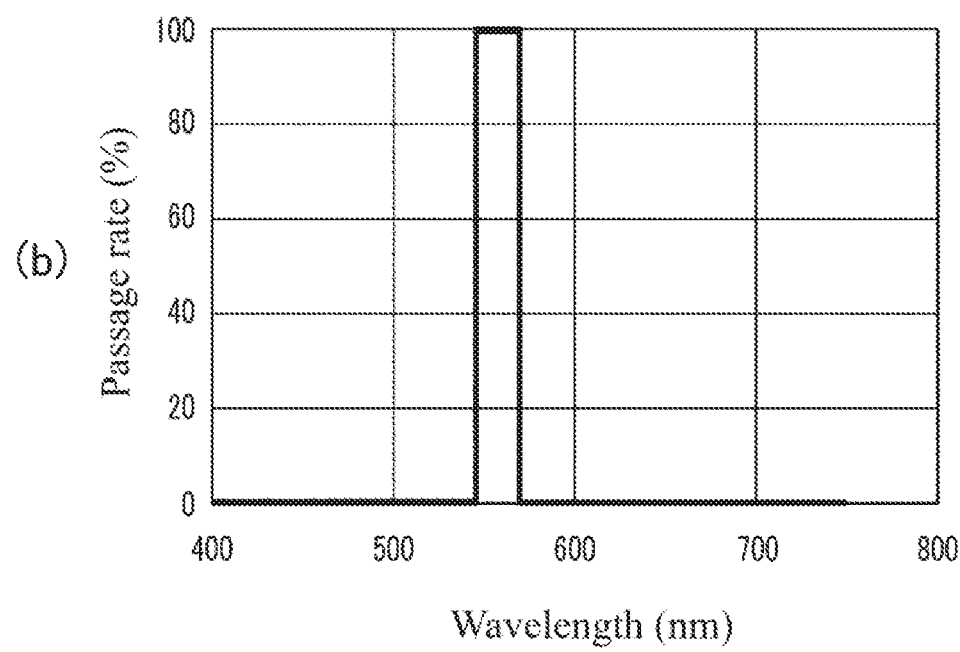

Also, the transmission spectrums of the optical filters 415 and 416 in the present embodiment are not limited to the spectrums shown in FIG. 9.

FIGS. 12(a) and 12(b) respectively show the transmission spectrums of an optical filter 415A and an optical filter 416A in a variation of the present embodiment. The optical filter 415A and the optical filter 416A are respectively used in place of the optical filter 415 and the optical filter 416. In FIGS. 12(a) and 12(b), the horizontal axis indicates the wavelength (nm), and the vertical axis indicates the transmittance (%).

The optical filter 415A has a transmission characteristic of allowing light in the wavelength region W1, the Wavelength region W2, and the wavelength region W7 (W band), and light with wavelengths longer than those the wavelength region WR shown in FIG. 1 to pass (be transmitted) with low loss. Specifically, the optical filter 415A has a transmission characteristic of allowing the passage of light in a wavelength region of wavelengths less than 502 nm, a wavelength region of wavelengths greater than or equal to 528 nm and less than 584 nm, and a wavelength region of wavelengths greater than or equal to 660 nm. Also, the optical filter 415A blocks light in a wavelength region of wavelengths greater than or equal to 502 nm and less than 528 nm, and a wavelength region of wavelengths greater than or equal to 584 nm and less than 660 nm.

The optical filter 416A has a transmission characteristic of allowing light in the wavelength region W2, the wavelength region W5 (N band), and the wavelength region WR shown in FIG. 1 to pass (be transmitted) with low loss. Specifically, the optical filter 416A has a transmission characteristic of allowing the passage of light in a wavelength region of wavelengths greater than or equal to 452 nm and less than 502 nm, a wavelength region of wavelengths greater than or equal to 546 nm and less than 570 nm, and a wavelength region of wavelengths greater than or equal to 620 nm and less than 660 nm. Also, the optical filter 416A blocks light in a wavelength region of wavelengths less than or equal to 452 nm, a wavelength region of wavelengths greater than or equal to 502 nm and less than 546 nm, a wavelength region of wavelengths greater than or equal to 570 nm and less than 620 nm, and a wavelength region of wavelengths greater than or equal to 660 nm.

As shown in FIG. 1, the light transmittance $T_{W1}$ of hemoglobin in the wavelength region W1 and the light transmittance $T_{W2}$ of hemoglobin in the wavelength region W2 vary linearly relative to the degree of oxygen saturation. Also, the extent of variation in the light transmittance $T_{W1}$ and the light transmittance $T_{W2}$ that accompanies a change in the degree of oxygen saturation is relatively high. Accordingly, a parameter that is dependent on the degree of oxygen saturation can be acquired by using the pixel values of B pixels obtained by irradiating the biological tissue with illumination light in the wavelength region W1 and the wavelength region W2 obtained using the optical filter 415A, and the pixel values of B pixels obtained by irradiating the biological tissue with illumination light in the wavelength region W2 obtained using the optical filter 416A. This parameter is used to correct the degree of oxygen saturation acquired in processing step S5, for example. Accordingly, the precision in detection of the degree of oxygen saturation improves.

Also, as shown in FIG. 2, the extent of variation in the spectral characteristics of the biological tissue relative to the extent of scattering is relatively large in the wavelength region W1 and the wavelength region W2. Also, the amount of variation in the spectral characteristics of the biological tissue relative to the extent of scattering is different between the wavelength region W1 and the wavelength region W2. For this reason, using the optical filter 415A and the optical filter 416A makes it possible to acquire a parameter that is dependent on the degree of oxygen saturation and also the extent of scattering.

Also, as shown in FIG. 1, in the wavelength region of wavelengths greater than or equal to 660 nm, the absorption of light by hemoglobin is small, and the light transmittance is high. Also, in the wavelength region of wavelengths greater than or equal to 660 nm, the amount of variation in the light transmittance of hemoglobin relative to change in the degree of oxygen saturation is relatively small. For this reason, by using the pixel values of R pixels obtained by irradiating the biological tissue with light in the wavelength region of wavelengths greater than or equal to 660 nm obtained using the optical filter 415A, it is possible to acquire biological information other than the total hemoglobin amount and the degree of oxygen saturation of the biological tissue as background information. Subtracting this background information from the pixel values makes it possible to improve the precision in detection of the total hemoglobin amount and the degree of oxygen saturation.

Figure 12:
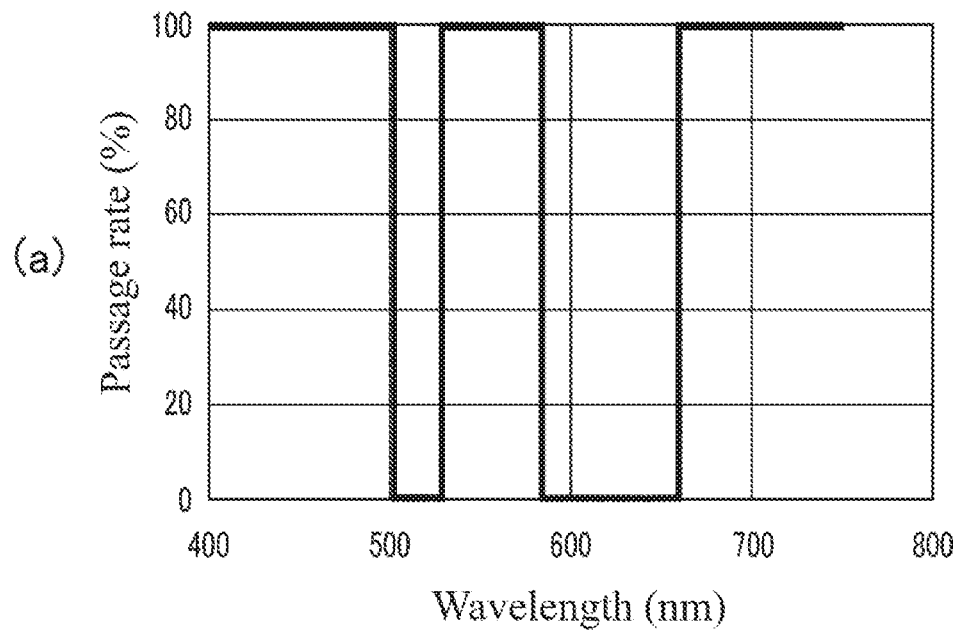
FIG. 12 shows transmission spectrums of optical filters according to a variation of the embodiment of the present disclosure.
Figure 12:
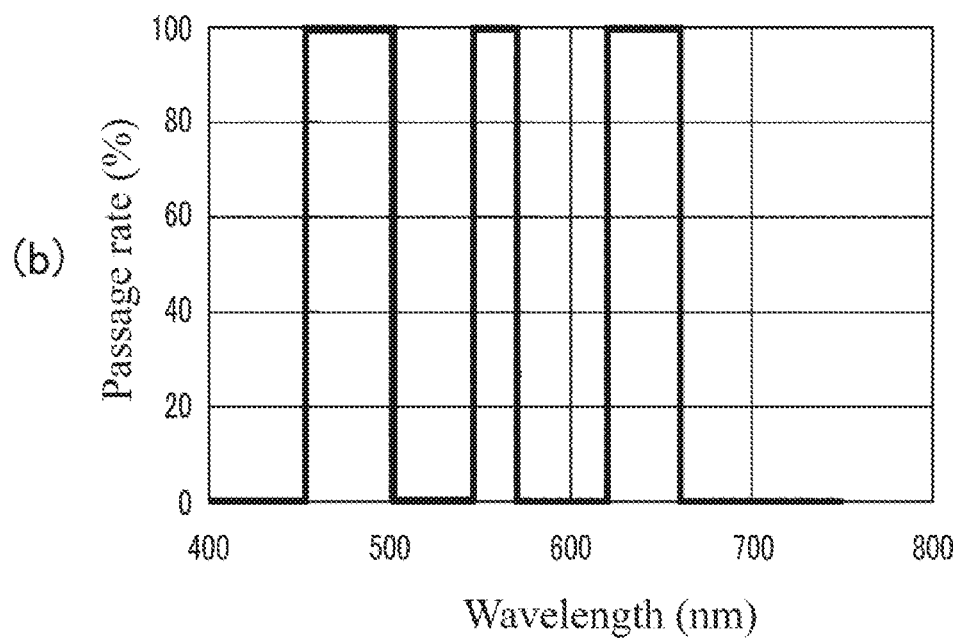

Note that the transmission spectrums of the optical filter 415A and the optical filter 416A are not limited to the characteristics shown in FIG. 12. For example, instead of having transmission characteristics of allowing light in the wavelength region W2 to pass, the optical filter 416A may have transmission characteristics of allowing the passage of light any wavelength region within the pass wavelength region of the B color filter. Also, instead of having transmission characteristics of allowing light with wavelengths greater than or equal to 660 nm to pass, the optical filter 415A may have transmission characteristics of allowing the passage of light in any wavelength region within the pass wavelength region of the R color filter.

Also, in the above embodiment, in processing step S2 shown in FIG. 10, color captured image data is generated based on the R digital image data R(x,y), the G digital image data W(x,y), and the B digital image data B(x,y) that are obtained using the first special light that passes through the optical filter 415, but the present disclosure is not limited to this. For example, a color captured image may be generated based on image data obtained using the second special light that passes through the optical filter 416A. Also, a color captured image may be generated based on both image data obtained using the first special light and image data obtained using the second special light. Furthermore, a configuration is possible in which a color captured image is generated based on image data obtained using the first special light, and a color captured image is also generated based on image data obtained using the second special light.

For example, in the case of using the optical filter 415A and the optical filter 416A as optical filters, the first special light and the second special light have different spectrums. For this reason, a color captured image generated using the first special light and a color captured image generated using the second special light have different hues. However, this difference in hue can be suppressed through image processing. Accordingly, by generating a color captured image based on image data obtained using the first special light, generating a color captured image based on image data obtained using the second special light, and adjusting the hues of the two color captured images, it is possible to display a color captured image of the biological tissue without reducing the frame rate.

Also, the image sensor 141 of the present embodiment is described as being an image sensor for color image capturing that includes R, G, and B primary-color color filters on the front side, but there is no limitation to this configuration, and an image sensor for color image capturing that includes Y, Cy, Mg, and G complementary-color color filters for example may be used.

Also, the image sensor 141 of the present embodiment is described as being an image sensor for color image capturing that includes an on-chip color filter 141a, but there is no limitation to this configuration, and a configuration is possible in which, for example, an image sensor for black-and-white image capturing is used and includes a so-called frame sequential color filter. Also, the color filter 141a is not limited to having an on-chip configuration, and can be arranged in the optical path between the light source 430 and the image sensor 141.

Also, in the above embodiment, a configuration is applied in which the rotating filter 410 is provided on the light source side and performs filtering on illumination light IL, but the present disclosure is not limited to this configuration, and a configuration is possible in which the rotating filter 410 is provided on the image sensor side (e.g., between the objective optical system 121 and the image sensor 141) and performs filtering on returning light from the subject.

Also, in the above embodiment, a white light source such as a xenon lamp is used as the light source that generates wide band light for illumination, but it is possible to use a light source that generates non-white wide band light having a sufficient light quantity over the entire pass wavelength region of the optical filters that are used.

Also, although transmissive optical filters are used in the above embodiment, reflective optical filters that reflect a pass wavelength region may be used.

Also, although the example of applying the present disclosure to an electronic endoscope, which is one aspect of a digital camera, is described in the above embodiment, the present disclosure can also be applied to systems that use various other types of digital cameras (e.g., digital SLR cameras or digital video cameras). For example, if the present disclosure is applied to a digital still camera, it is possible to observe body surface tissue or observe brain tissue during craniotomy (e.g., perform a rapid brain blood flow test).

The invention claimed is:

1. An analysis device comprising:
a light source device;
a wavelength selection unit that alternatively extracts first special light and second special light from light emitted from the light source device, the first special light and the second special light having mutually different spectrums;
an image sensor that includes an RGB color filter, receives light from a biological tissue that is a subject, and outputs a pixel signal that corresponds to the received light; and
a signal processing unit that performs predetermined signal processing on the pixel signal output from the image sensor,
wherein the first special light includes light in a first wavelength region that passes through a G filter of the RGB color filter,
the second special light includes light in a second wavelength region that passes through the G filter, the second wavelength region being different from the first wavelength region,
at least one of the first special light and the second special light includes light that passes through an R filter of the RGB color filter,
at least one of the first special light and the second special light includes light that passes through a B filter of the RGB color filter,
the signal processing unit calculates a first indicator that indicates a feature amount of the biological tissue, based on the pixel signal output according to the light in the first wavelength region and the pixel signal output according to the light in the second wavelength region, and
the signal processing unit generates a color captured image of the biological tissue based on the pixel signal output according to light that passes through the RGB color filter.

2. The analysis device according to claim 1,
wherein the feature amount is a degree of oxygen saturation of hemoglobin included in the biological tissue, and
the first indicator is a ratio N/W of a pixel signal N output from the image sensor according to the light in the first wavelength region and a pixel signal W output from the image sensor according to the light in the second wavelength region.

3. The analysis device according to claim 2,
wherein the first wavelength region includes a wavelength region that is defined by a predetermined pair of isosbestic points of hemoglobin, and
the second wavelength region includes a wavelength region that includes the first wavelength region and is defined by a pair of isosbestic points that is different from the predetermined pair of isosbestic points of hemoglobin.

4. The analysis device according to claim 3,
wherein the first wavelength region is a wavelength region of wavelengths greater than or equal to 546 nm and less than or equal to 570 nm, and
the second wavelength region is a wavelength region of wavelengths greater than or equal to 528 nm and less than or equal to 584 nm.

5. The analysis device according to claim 4,
wherein a wavelength region of light transmitted by the R filter includes a wavelength region of wavelengths greater than or equal to 600 nm,
a wavelength region of light transmitted by the G filter includes a wavelength region of wavelengths greater than or equal to 528 nm and less than or equal to 584 nm, and
a wavelength region of light transmitted by the B filter includes a wavelength region of wavelengths less than or equal to 502 nm.

6. The analysis device according to claim 2,
wherein the signal processing unit calculates a second indicator that indicates the amount of hemoglobin included in the biological tissue, using the following expression, based on the pixel signal W, a pixel signal R output from the image sensor according to light that passes through the R filter, and a pixel signal B output from the image sensor according to light that passes through the B filter, $$W/(C1 \times R + C2 \times W + C3 \times B)$$

where C1, C2, and C3 are each a constant greater than or equal to zero.

7. The analysis device according to claim 6,
wherein the first wavelength region includes a wavelength region that is defined by a predetermined pair of isosbestic points of hemoglobin, and
the second wavelength region includes a wavelength region that includes the first wavelength region and is defined by a pair of isosbestic points that is different from the predetermined pair of isosbestic points of hemoglobin.

8. The analysis device according to claim 7,
wherein the first wavelength region is a wavelength region of wavelengths greater than or equal to 546 nm and less than or equal to 570 nm, and
the second wavelength region is a wavelength region of wavelengths greater than or equal to 528 nm and less than or equal to 584 nm.

9. The analysis device according to claim 1,
wherein the signal processing unit generates a color captured image of the biological tissue based on a pixel signal R output from the image sensor according to light that passes through the R filter, a pixel signal G output from the image sensor according to light that passes through the G filter, and a pixel signal B output from the image sensor according to light that passes through the B filter, and
the pixel signal G is one of a pixel signal N output from the image sensor according to the light in the first wavelength region and a pixel signal W output from the image sensor according to the light in the second wavelength region.

10. The analysis device according to claim 9,
wherein the feature amount is a degree of oxygen saturation of hemoglobin included in the biological tissue, and
the first indicator is a ratio N/W of a pixel signal N output from the image sensor according to the light in the first wavelength region and a pixel signal W output from the image sensor according to the light in the second wavelength region.

11. The analysis device according to claim 10,
wherein the first wavelength region includes a wavelength region that is defined by a predetermined pair of isosbestic points of hemoglobin, and
the second wavelength region includes a wavelength region that includes the first wavelength region and is defined by a pair of isosbestic points that is different from the predetermined pair of isosbestic points of hemoglobin.

12. The analysis device according to claim 10,
wherein the signal processing unit calculates a second indicator that indicates the amount of hemoglobin included in the biological tissue, using the following expression, based on the pixel signal W, a pixel signal R output from the image sensor according to light that passes through the R filter, and a pixel signal B output from the image sensor according to light that passes through the B filter, $$W/(C1 \times R + C2 \times W + C3 \times B)$$

where C1, C2, and C3 are each a constant greater than or equal to zero.

13. The analysis device according to claim 1,
wherein the wavelength selection unit includes
a first optical filter that extracts the first special light from the light emitted from the light source device,
a second optical filter that extracts the second special light from the light emitted from the light source device, and
a filter drive unit that alternatively inserts the first optical filter and the second optical filter into a light path of the light emitted from the light source device.

14. A method of analysis comprising:
alternatively extracting first special light and second special light from light emitted from a light source device, the first special light and the second special light having mutually different spectrums;
receiving, by an image sensor that includes an RGB color filter, light from a biological tissue that is a subject;
outputting a pixel signal that corresponds to the received light; and
performing predetermined signal processing on the outputted pixel signal,
wherein the first special light includes light in a first wavelength region that passes through a G filter of the RGB color filter,
the second special light includes light in a second wavelength region that passes through the G filter, the second wavelength region being different from the first wavelength region,
at least one of the first special light and the second special light includes light that passes through an R filter of the RGB color filter,
at least one of the first special light and the second special light includes light that passes through a B filter of the RGB color filter,
wherein the performing predetermined signal processing includes calculating a first indicator that indicates a feature amount of the biological tissue, based on the pixel signal output according to the light in the first wavelength region and the pixel signal output according to the light in the second wavelength region, and
wherein the method includes generating a color captured image of the biological tissue based on the pixel signal output according to light that passes through the RGB color filter.

15. The method according to claim 14,
wherein the feature amount is a degree of oxygen saturation of hemoglobin included in the biological tissue, and
the first indicator is a ratio N/W of a pixel signal N output from the image sensor according to the light in the first wavelength region and a pixel signal W output from the image sensor according to the light in the second wavelength region.

16. The method according to claim 15,
wherein the performing predetermined signal processing includes calculating a second indicator that indicates the amount of hemoglobin included in the biological tissue, using the following expression, based on the pixel signal W, a pixel signal R output from the image sensor according to light that passes through the R filter, and a pixel signal B output from the image sensor according to light that passes through the B filter, $$W/(C1 \times R + C2 \times W + C3 \times B)$$

where C1, C2, and C3 are each a constant greater than or equal to zero.

17. The method according to claim 15,
wherein the first wavelength region includes a wavelength region that is defined by a predetermined pair of isosbestic points of hemoglobin, and the second wavelength region includes a wavelength region that includes the first wavelength region and is defined by a pair of isosbestic points that is different from the predetermined pair of isosbestic points of hemoglobin.

18. The method according to claim 17,
wherein the first wavelength region is a wavelength region of wavelengths greater than or equal to 546 nm and less than or equal to 570 nm, and
the second wavelength region is a wavelength region of wavelengths greater than or equal to 528 nm and less than or equal to 584 nm.

19. The method according to claim 18,
wherein a wavelength region of light transmitted by the R filter includes a wavelength region of wavelengths greater than or equal to 600 nm,
a wavelength region of light transmitted by the G filter includes a wavelength region of wavelengths greater than or equal to 528 nm and less than or equal to 584 nm, and
a wavelength region of light transmitted by the B filter includes a wavelength region of wavelengths less than or equal to 502 nm.

20. The method according to claim 14,
the method further comprising generating a color captured image of the biological tissue based on a pixel signal R output from the image sensor according to light that passes through the R filter, a pixel signal G output from the image sensor according to light that passes through the G filter, and a pixel signal B output from the image sensor according to light that passes through the B filter, and
the pixel signal G is one of a pixel signal N output from the image sensor according to the light in the first wavelength region and a pixel signal W output from the image sensor according to the light in the second wavelength region.

* * * * *